United States Patent [19]
Feith

[11] Patent Number: 5,991,667
[45] Date of Patent: Nov. 23, 1999

[54] PACING LEAD WITH POROUS ELECTRODE FOR STABLE LOW THRESHOLD HIGH IMPEDANCE PACING

[75] Inventor: Frederick Feith, Brummen, Netherlands

[73] Assignee: Vitatron Medical, B.V., Dieren, Netherlands

[21] Appl. No.: 08/966,916

[22] Filed: Nov. 10, 1997

[51] Int. Cl.[6] .................................................. A61N 1/05
[52] U.S. Cl. ......................... 607/120; 607/122; 607/126
[58] Field of Search ................................... 607/120–128; 600/373–375, 381

[56] References Cited

U.S. PATENT DOCUMENTS

| | | |
|---|---|---|
| 3,749,101 | 7/1973 | Williamson . |
| 4,030,508 | 6/1977 | Thalan . |
| 4,502,492 | 3/1985 | Bornzin . |
| 4,784,161 | 11/1988 | Skalsky et al. . |
| 4,844,099 | 7/1989 | Skalsky et al. . |
| 4,934,381 | 6/1990 | MacGregor . |
| 5,282,844 | 2/1994 | Stokes et al. ............................ 607/120 |
| 5,324,327 | 6/1994 | Cohen ..................................... 607/122 |
| 5,578,068 | 11/1996 | Laske et al. ............................. 607/126 |

OTHER PUBLICATIONS

Stokes et al., "A New Efficient NanoTip Lead," Pace, vol. 13, Dec. 1990, Part II, pp. 1901–1905.
Strokes, "Do Small Electrodes Have God Sensing?", Reblampa 78024–119, 198–200, 1995.
Brinker, "Endocardial Pacing Leads: The Good, The Bad, and the Ugly," Pace, vol. 18, May 1995, Part I, pp. 953–954.

Primary Examiner—Jeffrey R. Jastrzab
Attorney, Agent, or Firm—Thomas F. Woods; Harold Patton; Michael T. Taro

[57] ABSTRACT

A pacing lead, and system for pacing, where the lead has an improved distal tip designed to provide reliable chronic fixation of the electrode-heart interface, while also providing low pacing threshold. The distal end of the lead has a standard surface, of roughly hemispherical shape, made of a porous material. In one embodiment, the tip surface is suitably about 6–8 square mm, and there is a smaller surface of about 1.5–2.0 square mm which is electrically isolated from the remainder of the porous surface; the smaller surface acts as a high impedance electrode, providing low threshold, while the larger porous surface provides the stable fixation. A steroid source is housed in the distal end of the lead, so as to provide an eluted steroid to the electrode surface area, as well as at least part of the remaining porous surface, whereby the overall porous surface and the eluted steroid minimizes the resulting capsule of non-excitable tissue around the electrode, providing for a stable reduced threshold. In another embodiment, a switching network is provided, suitably in the pacemaker, for selectively connecting one or both portions as the active electrode for pacing and for sensing.

20 Claims, 2 Drawing Sheets

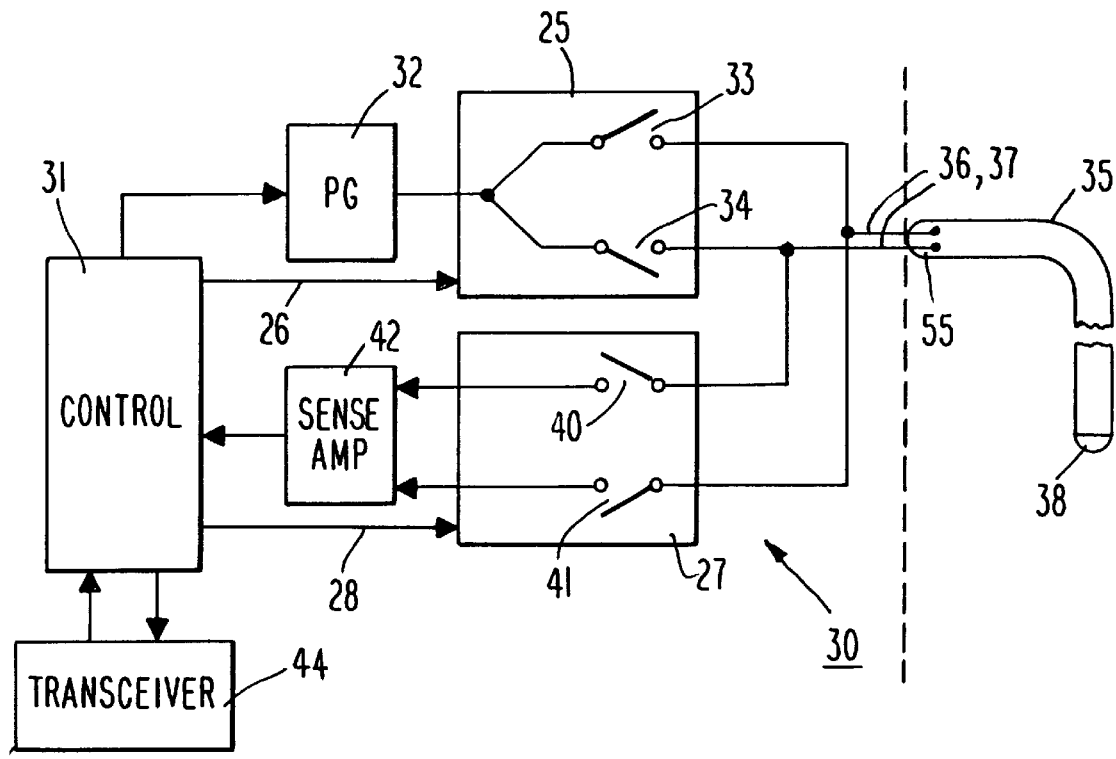
Fig. 1
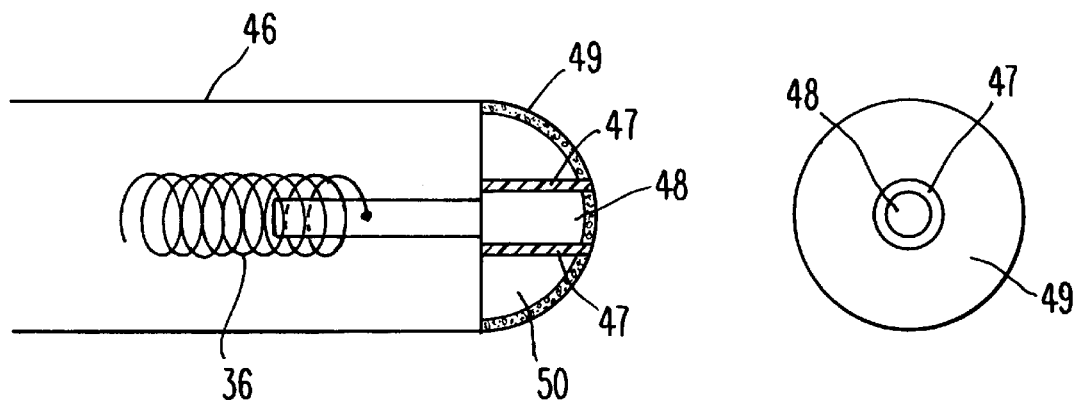
Fig. 2A
Fig. 2B

PACING LEAD WITH POROUS ELECTRODE FOR STABLE LOW THRESHOLD HIGH IMPEDANCE PACING

FIELD OF THE INVENTION

This invention relates to pacing systems having endocardial leads and, more particularly, systems with leads having porous tip electrode designs which provide stable chronic low pacing thresholds and good sensing characteristics.

BACKGROUND OF THE INVENTION

The importance of effective and reliable endocardial leads in modern pacing systems is well recognized. Advances in the design of implantable pacemaker units have been spectacular, resulting in an array of long-life pulse generators which can provide pacing in modes that can be selected for the patient, and re-programmed to adapt to changes in patient conditions. But the pacing system needs to interface with the patient's heart, both to deliver the generated stimulus pulses and to sense spontaneous cardiac signals. It is the pacing lead that provides this interface, and its reliability and performance must match that of the pulse generator in order to ensure overall system functionality over the lifetime of the pacemaker.

In delivering stimulus pulses from the pacemaker unit to the patient's heart, the lead must perform the functions of carrying the pulses the length of the lead, and then delivering them to the heart wall, i.e., the myocardial tissue. This must be done in a manner such that the resulting electric field evokes depolarization of the cardiac cells and thus produces a cardiac contraction, either ventricular or atrial. The first task, that of carrying the pulses, requires integrity of the conductor (or conductors, for a bipolar lead) as well as the insulation that surrounds the conductor. The second task is complex. For a unipoloar or bipolar lead, an electrode is positioned at the distal tip, to provide an optimal electrode-myocardial interface. This interface must provide a good electrical connection, but in order to achieve this, a good mechanical connection must be provided in order that the electrode is well fixed, or anchored, with respect to the myocardium so as to provide stable chronic delivery of the stimulus pulses. Many anchoring mechanisms have been developed for employment at the distal end of endocardial leads, probably the most successful of which is the use of tines which engage the traebaculae and thus hold the distal tip in place. However, a further advance was provided by the development of the porous metal coated electrode. Such electrodes have a porous, or micro-porous surface which, when nestled against the heart wall, allows fibrous tissue ingrowth, resulting in stable long term fixation. Also, and importantly, the fibrous growth into the porous surface provides anchoring which reduces mechanical movement. In turn, this reduces the growth of connective tissue around the electrode surface which occurs as a reaction to the foreign body electrode, thus resulting in a reduced connective tissue "capsule" between the electrode surface and the excitable myocardial muscle. This is of great importance, as the capsule is not excitable, and acts as an effective extension of the distance between the electrode surface and the myocardial cells, which adversely affects both pacing threshold and sensing.

The importance of the porous surface is illustrated by considering the electric field strength established by a pulse of voltage V which is delivered to the electrode surface. For a spherical electrode, the field strength is inversely proportional to the square of (r+d), where r is the radius of the spherical electrode and d is the distance from the electrode surface to the boundary of the fibrous capsule and the undamaged myocardium. Thus, for a stimulus pulse of a voltage V, the field strength is reduced significantly by capsule thickness; stating the matter in an alternate way, the reduction of the capsule thickness by a porous surface provides a substantial improvement in pacing threshold. Capsule formation has been further reduced by the use of steroid elution, whereby a material which suppresses the myocardial/electrode interface reaction is eluted through the electrode surface, resulting in a lessened threshold rise as the electrode becomes fixed with respect to the myocardium.

Another important characteristic of the electrode is that of electrode impedance, i.e., the ratio of pulse voltage to the current drain at the electrode surface. Pacing impedance is inversely proportional to electrode surface area. Since it is desirable to provide a moderately high pacing impedance to reduce current drain while providing good power transfer, electrode surface should be as small as possible, although in practice there is an optimum surface size related to the thickness of the connective tissue capsule. Stokes et al developed the "Nano Tip" lead, which combines deep porosity, steroid elution, and a low surface area down to about 1.5 square mm. Stokes K, Bird T, "A New Efficient Nano Tip Lead", *PACE,* 1990; 13 (Part II): 1901–1905. This lead provides low pacing thresholds, and a pacing impedance in the range of about 1 to 1.2 Kohm, compared to an impedance of about 600 ohm for conventional electrodes of about 6–8 square mm surface. Additionally, Stokes showed that such small electrodes can provide good sensing, because of the high input impedance relative to the sensing impedance of the porous surface electrode. See Stokes K., "Do small electrodes have good sensing?", *Reblampa.* 1995; 8: 198–200. For good sensing, the source impedance should be small, so as to avoid attenuation when the sensed signal is connected to the input of a sense amplifier, which desirably has a high input impedance. While a larger electrode surface in principle provides a better (smaller) source impedance than a smaller surface, more porous surfaces also provide smaller source impedance; microporous surfaces provide even better sensing than porous surfaces.

However, the small surface electrode does not provide as much porous surface for tissue ingrowth as the larger surface, and this can present stability problems. Specifically, for a porous surface which is much smaller than the prior standard of 6–8 mm, there are indications that the stability of the electrode fixation may not be enough to guarantee clinical safety. Stable fixation is a key to maintaining a thin capsule and chronic low threshold, and accordingly there remains a need for improvement in electrode design which will provide the necessary stable electrode/heart wall interface, consistent with optimally reliable and stable thresholds, good sensing, and high pacing impedance.

SUMMARY OF THE INVENTION

It is an object of this invention to provide a pacing lead which combines the features of relatively high pacing impedance, chronic low pacing threshold and good sensing, while also providing the maximum available stability of lead placement. It is a further object to provide a pacing system wherein the impedance and threshold characteristics of the lead tip electrode can be programmably selected to optimize performance for the patient in whom the pacing system is implanted.

Accordingly, there is provided a pacing lead having a tip which combines a small porous surface pacing electrode to provide relatively high pacing impedance, and a another porous surface which is electrically isolated from the pacing surface, suitably positioned annularly around the centrally located electrode surface. The tip is combined with a mechanism for eluting of a steroid or other material to both the electrode surface and at least a portion of the remaining porous surface adjacent the pacing surface, in order to reduce non-excitable tissue growth at and around the vicinity of the pacing electrode. The tip preferably has a substantially hemispherical surface, and the relatively large combined porous surface and the eluting capacity provide maximum chronic fixation with a minimized tissue capsule around the pacing electrode, thereby providing the desired high pacing impedance and low pacing threshold.

The invention embraces a pacing system which combines the lead as described above together with a pacemaker. The pacemaker is programmable and may provide any of the well known features of modern pacemakers. Important to this invention, the lead may have separate conductors which electrically connect the respective portions of the porous tip surface to the pacemaker. The pacemaker has a switching network, programmable from an external programmer, for selecting the desired connection of tip surfaces to the pacemaker, for the pacing and sensing functions. Thus, the system can be operated using only one electrode surface, either the annular ring or the portion located at the axial center of the porous tip surface, for both pacing and sensing; or both sections can be used for these functions; or one section (the smaller section) can be used for pacing, while the other (the larger section) can be used for sensing. This selectivity feature provides the ability to match the pacing and sensing characteristics to the patient.

BRIEF DESCRIPTION OF THE DRAWINGS

FIG. 1 is a system diagram, illustrating a pacemaker in combination with a pacing lead in accordance with this invention, the diagram showing the primary features of the pacemaker which are important for illustrating this invention.

FIG. 2A is a diagrammatic cross sectional view of the distal end of a pacing lead in accordance with this invention; FIG. 2B is an end view of the distal tip of the pacing lead illustrated in FIG. 2A.

DESCRIPTION OF THE PREFERRED EMBODIMENTS

Figure 3:
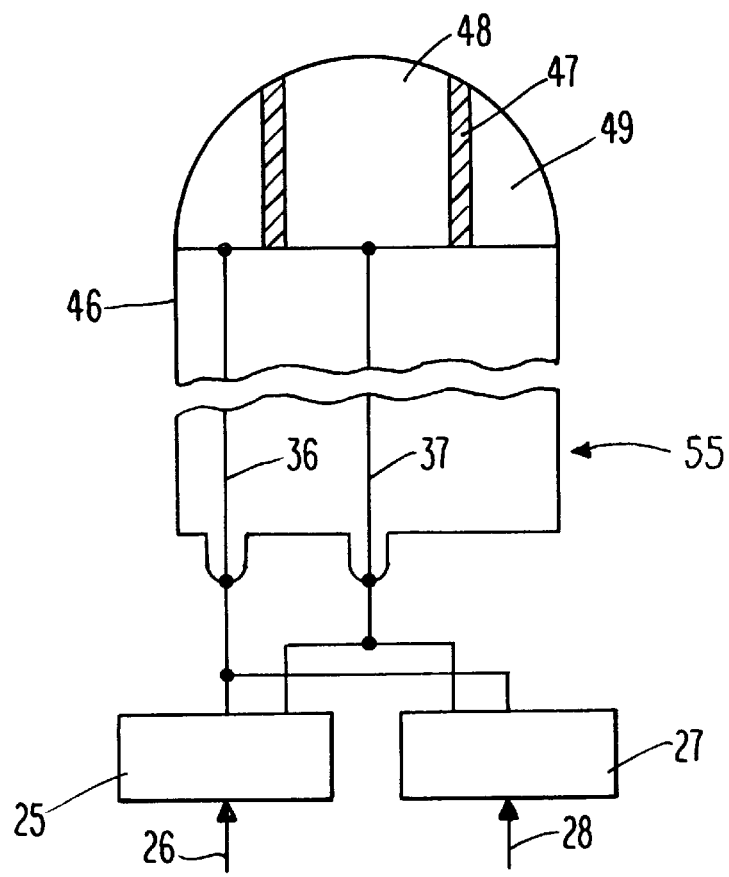
FIG. 3 is a cross sectional sketch of a distal tip of a lead in accordance with this invention, showing separate electrical connections to the inner and outer portions of the tip surface.

Referring now to FIG. 1, there is shown a system diagram of a pacing system in accordance with this invention. The two basic components of a pacing system are, of course, a pacemaker as indicated at 30, and a lead as indicated at 35. The lead has a distal tip surface, as shown at 38, and one or more conductors as shown at 36,37 for conducting signals between the distal end and the proximal end, the latter being connected to the pacemaker. As is known, a pacing lead may be unipolar or bipolar; in this specification, the ring electrode which is proximal to the distal electrode in a bipolar lead is not illustrated, but it is understood that the invention is equally applicable to leads that have one or even more than one additional electrode proximal to the lead tip.

The pacemaker 30 has the conventional components as are used in modern pacemakers to carry out the primary function of generating and delivering pacing pulses, as well as the logic and timing circuits required to operate in the desired mode or modes. As illustrated, the logic and timing circuits are included in block 31, designated control, which suitably includes a microprocessor and memory for holding software instructions and data. A transceiver 44 is provided to transmit data to an external programmer, and to receive program instructions from the programmer, in a well known fashion. The pacing pulses, or stimuli, are generated by generator 32, subject to timing signals received from control 31. The generated pulses are delivered through switch block 25 to one or both of lead conductors 36,37, to connect the pulses to one or two tip surfaces, as discussed further below. The lead may be a conventional pacing lead, having two conductors running the length of the lead, and encapsulated by a protective casing, or tube. Cardiac signals that are sensed by the lead portion in the patient's heart, either between the tip electrode and the pacemaker case for a unipolar system or between the tip electrode and a ring electrode for a bipolar system, are connected through switch block 27 to a sense amplifier 42, where the detected signals are amplified and processed, and connected to control 31 for use in establishing pacemaker timing, collection of data, etc.

In practice, the setting of the switches 33,34 controls what portion or portions of the tip surface act as an electrode to deliver stimulus pulses, while switches 40,41 control what portion or portions of the tip surface are used to sense patient cardiac signals, as is discussed in greater detail in connection with FIG. 3. The settings of the switches are done by control signals from block 31; signals on line 26 control the settings of switches 33,34, while signals on line 28 control the settings of switches 40,41. While the selection is illustrated by switches housed in the pacemaker, it is to be understood that the invention contemplates incorporation of switches housed in the lead, suitably near the distal end.

Referring now to FIGS. 2A and 2B, there is illustrated a portion of the distal end of a lead in accordance with this invention. Within casing 46 there is shown a coiled conductor 36, which is mechanically and electrically attached to a tip portion 50, which is suitably substantially hemispherical and composed of a porous material. Tip portion 50 is preferably made of a rigid conductive material, which presents advantages after the tissue ingrowth into the porous surface. Although the drawing shows portion 50 as one integral piece, it is to be understood that only the outer surface need be porous; also, while not shown, tip portion 50 allows for steroid elution through to the surface. As used herein, the term porous refers to any of the standard porous type surfaces used in modern pacing electrodes, and includes what are referred to as microporous surfaces, any of which provide a microscopic surface area that enables tissue ingrowth and good chronic fixation. In the embodiment of FIG. 2A, tip portion 50 is divided into a center, or axial section having a surface 48, and an annular section which presents a surface 49, the two sections being divided by a cylinder of electrically insulating material shown at 47. In the embodiment illustrated, the inner center surface is the smaller surface, and only the center part of the tip surface is used as an electrode. Alternately, annular surface portion 49 may be of approximately equal size; or it may be the smaller portion, having an area of only about 1.5 to 2.0 square mm, and be used as the electrode. However, in any one of these embodiments the entire hemispherical surface, excluding the small portion taken up by the insulation 47, is useful for purposes of fixation. By way of example, the overall surface made up of 48,49 may be on the order of 6–8 square mm, while the electrode surface portion is only around 1.5–2.0 sq. mm. The geometry of FIG. B is preferred, but it is to be understood that the center surface portion need not be circular, and the outer portion 49 need not be annular, as illustrated. Also, while the invention is illustrated with just two surface portions divided by the insulation 47, there may more than two such portions. In all such cases, there is provided at the distal tip a surface electrode of desirably small area, to provide high pacing impedance, and a larger porous surface to provide the much needed long term fixation, which yields chronic stability. While the tip surface is suitably hemispherical, other geometric surfaces are equally within the scope of the invention.

Referring now to FIG. 3, there is illustrated an embodiment where there are provided respective different electrical connections to portions 48,49 of the tip. Lead conductor 37 is shown as being connected to center portion 48, while conductor 36 is connected to annular portion 49. (Another conductor, not shown, would be employed for a bipolar lead.) The conductors are electrically connected to the pacemaker at the lead proximal end 55, and connected to switch blocks 25, 27, as discussed above. Selection of the switches in blocks 25, 27 controls which portion or portions of the tip are used for pacing and sensing, respectively. For example, the center portion 48 may be used alone for pacing, while the outer portion 49 is used for sensing, depending on programmed instructions. Alternately, either one or both portions may be used for both pacing and sensing. The use of annular ring portion 49 as the electrode for both pacing and sensing has the advantage that the wider radial dimension, assuming the same small surface of only about 1.5 square mm, provides better sensing and equally good low threshold pacing.

Figure 4:
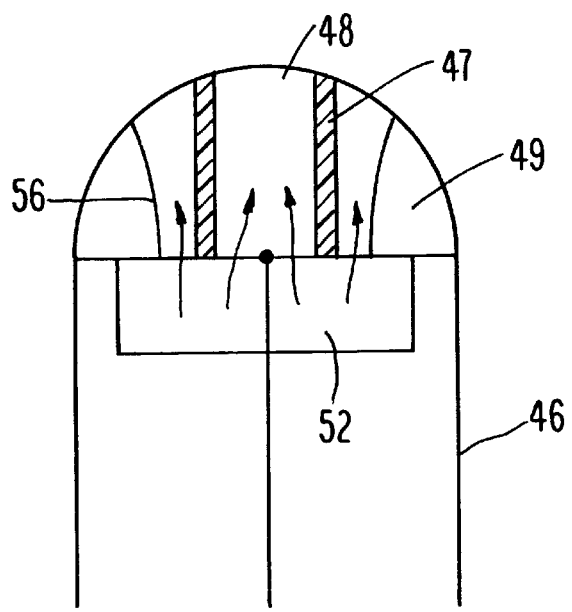
FIG. 4 is a cross sectional sketch of a distal tip of a lead in accordance with this invention, showing the positioning of a source of eluting steroid or other eluting material, and the inpact on the reduction of the non-excitable tissue capsule in the vicinity of the active electrode surface.

Referring now to FIG. 4, there is shown a diagrammatic sketch of a distal end of a lead in accord with this invention, where steroid elution is utilized. A block or reservoir 52 is shown diagrammatically at 52, positioned to provide the steroid, or eluant, to both portion 48 and to part of portion 49 sectioned off by liner or membrane 56. Here, only portion 48 is used as an electrode, but the steroid is eluted into at least of portion of the surrounding porous surface. It is know that elution of a steroid such as glucocorticosteroid at the electrode-tissue interface reduces and stabilizes the non-excitable capsule, providing better chronic threshold. See the above referenced Stokes et al article, PACE, December 1990, Part II. By releasing the steroid into the interface around the electrode, and not just at the electrode, there is provided the possibility of an enhancement of the steroid effect in terms of reducing the capsule that builds up at the electrode surface, and providing better thresholds.

What is claimed is:

1. A pacing lead for delivering pacing pulses to a patient's heart from a pacemaker and for sensing cardiac signals from said patient's heart and delivering said sensed cardiac signals to said pacemaker, comprising:

a lead body with a proximal end and a distal end, said lead body having conductive means for conducting said pacing pulses from said proximal end to said distal end and for conducting said sensed cardiac signals from said distal end to said proximal end;

a tip said distal end with an overall tip surface, said tip surface having first and second portions made of a porous material for engaging the inner heart wall and insulating means for electrically isolating said first and second portions, said first portion being axially located and constructed from a conductive material and said second portion being annularly positioned around said first portion; and connecting means for connecting at least one of said first and second portions to said conductive means, said connecting means has means for connecting only said first portion to said conductive means, whereby said first portion is connected as an electrode and said second portions is not active as an electrode.

2. The lead as described in claim 1, wherein said overall tip surface is a substantially hemispherical surface having an area of at least about 6–8 square mm.

3. The lead as described in claim 2, wherein said first portion has a surface area no greater than about 2.0 square mm.

4. The lead as described in claim 2, wherein said second portion has a surface no greater than about 2.0 square mm, and said connecting means has means for connecting only said second portion to said conductive means, whereby said second portion is connected as an electrode and said first portion is not active as an electrode.

5. The lead as described in claim 1, wherein said tip is made of a rigid material.

6. The lead as described in claim 1, wherein said connecting means comprises means for connecting said first and second portions commonly to said conductive means, whereby said first and second portions function together as a common pacing and sensing electrode.

7. The lead as described in claim 1, wherein said conductive means comprises first and second conductive paths, and said connecting means comprises means for connecting said first portion to said first path and second portion to said second path, whereby said portions can be connected as respective pacing and sensing electrodes.

8. The lead as described in claim 7, wherein said connecting means further comprises selection means for selecting which of said first and second portions are connected to said conductive means.

9. The lead as described in claim 1, wherein said insulating means has a surface area which is less than 10% of said hemispherical surface area.

10. The lead as described in claim 1, wherein said first and second portion have a combined surface area of 6–8 square mm, and said first portion has a surface of no greater than 2 square mm.

11. A cardiac pacing system, comprising:

a pacemaker having pulse means for generating pacing pulses, and sense means for receiving sensed cardiac signals;

a lead for delivering said pacing pulses to the patient's heart and for sensing cardiac signals and delivering said sensed cardiac signals to the pacemaker, said lead having a proximal end for connection to said pacemaker, a distal end, conductive means between said proximal and distal ends for conducting said pulses and said sensed cardiac signals, and a tip electrode at said distal end, said tip electrode having a surface for interfacing with the patient's heart wall, said tip surface having first and second surface areas, insulating means for electrically isolating said first and second surfaces, and connecting means for connecting said first surface to said conductive means; and said pacemaker further having selective connecting means for selectively connecting said pacemaker to said conductive means so that said first surface delivers said pacing pulses, and so that said sense means receives said sensed cardiac signals from said first surface.

12. The system as described in claim 11, wherein said lead comprises first and second conductors extending from the tip proximal end to the tip distal end, and said selective connecting means comprises switch means for connecting selected ones of said first and second conductors to said pulse means and to said sense means.

13. The pacing system as described in claim 11, wherein said tip surface comprises a porous material.

14. A pacing lead for delivering pacing pulses from a cardiac pacemaker to a patient's heart, and for sensing patient cardiac signals and delivering said signals to the pacemaker, said lead having a proximal end, a distal end, and a length therebetween, and conductive means for conducting said pulses and said sensed signals respectively along said length, said lead further having a tip configuration at said distal end, said tip configuration comprising:

a substantially hemispherical overall tip surface area, said tip surface area having a porous surface material;

a first surface area within said overall tip area, centered substantially at the axial center of said tip area, a second surface area within said overall tip area and positioned around said first area, and insulating means for electrically insulating said first and second areas from each other;

eluting means for eluting an eluant to one of said first and second surface areas and at least a portion of said other of said first and second surface areas; and connecting means for connecting only said one surface areas to said conductive means.

15. The lead as described in claim 14, wherein said second surface area is annular around said first surface area, and said eluting means elutes eluant to substantially all of said first and second surface areas.

16. The lead as described in claim 14, wherein said connecting means comprises first means for connecting said first surface area to said conductive means.

17. The lead as described in claim 14, wherein said connecting means comprises second means for connecting said second surface area to said conductive means.

18. The lead as described in claim 14, wherein said first surface is no greater than about 2 square mm, and said overall surface area is at least about 6 square mm.

19. The lead as described in claim 14, wherein said first and second surface areas are of substantially equal size.

20. The lead as described in claim 14, wherein said insulating means comprises a surface area which is less than 10% of said overall tip surface area.

* * * * *